US010898440B2

(12) United States Patent
Cade et al.

(10) Patent No.: US 10,898,440 B2
(45) Date of Patent: *Jan. 26, 2021

(54) BULK ENTERIC CAPSULE SHELLS

(71) Applicant: Capsugel Belgium NV, Bornem (BE)

(72) Inventors: Dominique Nicolas Cade, Colmar (FR); Hugues Straub, Colmar (FR)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/660,714

(22) Filed: Oct. 22, 2019

(65) Prior Publication Data
US 2020/0054569 A1  Feb. 20, 2020

Related U.S. Application Data

(62) Division of application No. 13/827,523, filed on Mar. 14, 2013, now Pat. No. 10,463,625.

(60) Provisional application No. 61/641,485, filed on May 2, 2012, provisional application No. 61/641,505, filed on May 2, 2012.

(51) Int. Cl.
| *A61K 9/48* | (2006.01) |
| *A61K 47/10* | (2017.01) |
| *B29C 41/14* | (2006.01) |
| *A61J 3/07* | (2006.01) |
| *B29L 31/00* | (2006.01) |

(52) U.S. Cl.
CPC .......... *A61K 9/4816* (2013.01); *A61K 9/4833* (2013.01); *A61K 47/10* (2013.01); *B29C 41/14* (2013.01); *A61J 3/077* (2013.01); *B29L 2031/7174* (2013.01)

(58) Field of Classification Search
CPC .... A61K 9/4816; A61K 47/10; A61K 9/4833; B29C 41/14; B29L 2031/7174; A61J 3/077
USPC .......................... 424/494; 514/781; 264/301
See application file for complete search history.

(56) References Cited

U.S. PATENT DOCUMENTS

| 2,718,667 A | 9/1955 | Malm et al. |
| 3,493,407 A | 2/1970 | Greminger, Jr. et al. |
| 3,617,588 A | 11/1971 | Langman |
| 3,740,421 A | 6/1973 | Schmolka |
| 4,001,211 A | 1/1977 | Sarkar |
| 4,111,202 A | 9/1978 | Theeuwes |
| 4,138,013 A | 2/1979 | Okajima |
| 4,539,060 A | 9/1985 | Wittwer et al. |
| 4,656,066 A | 4/1987 | Wittwer |
| 5,264,223 A | 11/1993 | Yamamoto et al. |
| 5,508,276 A | 4/1996 | Anderson et al. |
| 5,756,123 A * | 5/1998 | Yamamoto ........... A61K 9/4816 424/451 |
| 5,851,579 A | 12/1998 | Wu et al. |
| 5,910,319 A | 6/1999 | Anderson et al. |
| 6,515,008 B1 | 2/2003 | Tiongson et al. |
| 8,372,836 B2 | 2/2013 | Ketner et al. |
| 8,710,105 B2 | 4/2014 | Son et al. |
| 9,044,406 B2 | 6/2015 | Son et al. |
| 9,452,141 B1 | 9/2016 | Chang et al. |
| 10,463,625 B2 * | 11/2019 | Cade .................... A61K 9/4816 |
| 2007/0098786 A1* | 5/2007 | Chidambaram ..... A61K 9/4816 424/456 |
| 2007/0298095 A1 | 12/2007 | Nagata et al. |
| 2012/0161364 A1* | 6/2012 | Son ....................... A61K 47/38 264/306 |
| 2013/0287840 A1 | 10/2013 | Benameur |
| 2013/0295188 A1 | 11/2013 | Cade et al. |
| 2015/0010620 A1 | 1/2015 | Benameur et al. |
| 2015/0050334 A1 | 2/2015 | Cade et al. |
| 2015/0132372 A1 | 5/2015 | Benameur et al. |
| 2017/0157058 A1 | 6/2017 | Chang et al. |
| 2019/0240160 A1 | 8/2019 | He et al. |

FOREIGN PATENT DOCUMENTS

| CA | 2870134 | 11/2013 |
| CA | 2870033 | 4/2017 |
| CA | 3031554 | 1/2018 |
| CN | 109661226 | 4/2019 |
| EP | 0401832 | 12/1990 |
| EP | 0648487 | 4/1995 |
| EP | 1447082 | 8/2004 |
| EP | 2476439 | 7/2012 |
| EP | 3178473 | 6/2017 |
| EP | 3272340 | 1/2018 |
| EP | 2844297 | 8/2018 |
| EP | 3446713 | 2/2019 |
| EP | 2844296 | 3/2019 |

(Continued)

OTHER PUBLICATIONS

Extended Search Report for European Application No. 16191168.0, dated Nov. 30, 2016.
International Search Report and Written Opinion for PCT/US2017/043012, dated Jan. 4, 2018.
ShinEtsu (AQOAT, Hypromellose Acetate Succinate, [Retrieved from internet <URL:http://www.metolose.jp/e/pharmaceutical/aqoat.shtml >], (Copyright 2001-2013), 1 page, plus 3 pages from the internet archive to further document the particle size back to 2008; total 4 pages).
Felton et al., "Enteric Coating of Gelatin and Cellulosic Capsules Using an Aqueous-Based Acrylic Polymer," *Pharm. Sci*, Abstract T3320 (2002).

(Continued)

*Primary Examiner* — Blessing M Fubara
(74) *Attorney, Agent, or Firm* — Klarquist Sparkman, LLP

(57) ABSTRACT

The present disclosure relates to aqueous composition comprising hydroxypropyl methyl cellulose acetate succinate (HPMCAS) polymer dispersed in water, wherein the dispersed polymer is partially neutralized with at least one alkaline material. The instant disclosure also relates to compositions for use in methods of making capsule shells endowed with bulk enteric properties. The present disclosure also relates to capsules made according with the compositions and methods of the present disclosure.

17 Claims, No Drawings

(56) References Cited

FOREIGN PATENT DOCUMENTS

| | | |
|---|---|---|
| EP | 3487487 | 5/2019 |
| EP | 3524271 | 8/2019 |
| GB | 1310697 | 3/1973 |
| JP | S58-138458 | 8/1983 |
| JP | H03-279325 | 12/1991 |
| JP | H07-109219 | 4/1995 |
| JP | 2004-131474 | 4/2004 |
| JP | 2006-016372 | 1/2006 |
| JP | 5890428 | 3/2016 |
| JP | 2018058870 | 4/2018 |
| JP | 6397813 | 9/2018 |
| JP | 2019527223 | 9/2019 |
| JP | 6626712 | 12/2019 |
| TW | 200520790 | 7/2005 |
| TW | 1587880 | 6/2017 |
| WO | WO00/18377 | 4/2000 |
| WO | WO2004/030658 | 4/2004 |
| WO | WO2006/082842 | 8/2006 |
| WO | WO2008/050209 | 5/2008 |
| WO | WO2008/119943 | 10/2008 |
| WO | WO2009/050646 | 4/2009 |
| WO | WO2009/138920 | 11/2009 |
| WO | WO2011/030952 | 3/2011 |
| WO | WO2011/155686 | 12/2011 |
| WO | WO2012/053703 | 4/2012 |
| WO | WO2012/056321 | 5/2012 |
| WO | WO2013/164122 | 11/2013 |
| WO | WO2015/179072 | 11/2015 |
| WO | WO2018/017799 | 1/2018 |

OTHER PUBLICATIONS

Felton, L.A. et al., "Enteric Film Coating of Soft Gelatin Capsules," *Drug Development and Delivery*, 3(6), (Sep. 2003, posted Mar. 28, 2008).

Fisher Scientific (Ammonium Hydroxide, [Retrieved from Internet <URL: https://www.fishersci.com/us/en/catalog/search/products?keyword=ammonium+hydroxide&nav= >], [Downloaded Sep. 12, 2016], 7 pages).

Han et al., "In Vitro and In Vivo Evaluation of a Novel Capsule for Colon-Specific Drug Delivery," *Journal of Pharmaceutical Science*, 98(8):2626-2635 (Aug. 2009).

Hutchison, K. G. et al., "Soft gelatin capsules," in Aulton's Pharmaceutics: The Design & Manufacture of Medicine, Ch. 35, pp. 527-538, edited by Aulton, M., third edition (2001).

Huyghebaert et al., "Alternative method for enteric coating of HPMC capsules resulting in ready-to-use enteric-coated capsules," *Eur J Pharm Sci*, 21(5):617-623 (Apr. 2004).

International Search Report and Written Opinion for PCT/EP2013/055298 (dated Sep. 11, 2013).

Kirilmaz L., "Two new suggestions for pharmaceutical dosage forms : ethylcellulose and cellulose acetate phthalate capsules," *S.T.P., Pharma Science*, 3(5):374-378 (Nov. 1993).

Office Action from the Japanese Patent Office for Japanese Patent Application No. 2015-509338 (w/English translation) (dated Nov. 8, 2016).

Restriction Requirement from the United States Patent and Trademark Office for U.S. Appl. No. 13/827,523, dated Jul. 2, 2014.

Sigma-Aldrich (Ammonium Hydroxide product list, [Retrieved from Internet <URL: http://www.sigmaaldrich.com/catalog/search?term=ammonium+hydroxide&interface=All&N=O&lang=en&region=US&focus=product# >], [Retrieved Sep. 12, 2016], 3 pages).

Sigma-Aldrich (Sigma-Aldrich, Ammonium Hydroxide Solution, [Retrieved from internet <URL: http://www.sigmaaldrich.com/catalog/product/sial/338818?lang=en&region=US >], [Downloaded Jun. 18, 2016], 4 pages).

Thoma et al., "Enteric coated hard gelatin capsules," *Capsugel Technical Bulletin 1986*, 17 pages.

Restriction Requirement from the United States Patent and Trademark Office for U.S. Appl. No. 16/318,652, dated Jan. 28, 2020.

Office Action from the European Patent Office for European Application No. 18188242.4 (dated Apr. 17, 2019).

Office Action from the United States Patent and Trademark Office for U.S. Appl. No. 16/318,652, dated May 1, 2020.

Extended Search Report for European Application No. 19162194.5, dated Jun. 13, 2019.

Office Action from the Japanese Patent Office for Japanese Patent Application No. 2017-225773 (w/English translation) (dated Sep. 4, 2018).

\* cited by examiner

BULK ENTERIC CAPSULE SHELLS

This is a Divisional of U.S. patent application Ser. No. 13/827,523, filed Mar. 14, 2013, which claims the benefit of U.S. Provisional Application No. 61/641,505, filed May 2, 2012, and to U.S. Provisional Application No. 61/641,485, filed May 2, 2012, all of which are hereby incorporated by reference.

The present disclosure relates to aqueous compositions for use in the manufacture of capsule shells endowed with bulk enteric properties. The present disclosure also relates, in part, to HPMCAS partially neutralized in aqueous dispersions suitable for the implementation of said manufacturing process, and to enteric capsule shells and hard capsules obtained therewith.

Capsules are well-known dosage forms that normally consist of a shell filled with one or more specific substances. The shell itself may be a soft or a hard stable shell. Hard capsule shells are generally manufactured using dip moulding processes, which can be distinguished into two alternative procedures. In the first procedure, capsules are prepared by dipping stainless-steel mould pins into a solution of polymer, optionally containing one or more gelling agents (e.g. carrageenans) and co-gelling agents (e.g. inorganic cations). The mould pins are subsequently removed, inverted, and dried to form a film on the surface. The dried capsule films are then removed from the moulds, cut to the desired length, and then the caps and bodies are assembled, printed, and packaged. See e.g., U.S. Pat. Nos. 5,264,223, 5,756,123, and 5,756,123.

In the second procedure, no gelling agents or co-gelling agents are used and film-forming polymer solution gelifications on the moulding pins are thermally induced by dipping pre-heated moulding pins into the polymer solution. This second process is commonly referred to as thermogellation or thermogelling dip moulding. See, e.g., EP 0401832, U.S. Pat. Nos. 3,493,407, 4,001,211, GB1310697, U.S. Pat. No. 3,617,588 and WO 2008/050209. In each of the aforementioned processes, both utilize a solution of the different ingredients that constitute the capsule shell wall.

Methods for the manufacturing of the soft capsule shells are known in the art. See e.g. Aulton, M., Aulton's *Pharmaceutics: The Design & Manufacture of Medicines*, 527-533 (Kevin M G Taylor ed. 3$^{rd}$ ed. 2001).

Once the capsules are formed, different techniques have been used to impart enteric properties to the hard or soft capsule shells. One such technique involves treating the surface of the pre-manufactured capsules (e.g. spraying or film-coating already manufactured capsules) with one or more layers of a substance or composition that is known to impart enteric properties. However, this technique is time-consuming, complex, and consists of expensive multiple step process. In addition, hard capsule shells made by this process must typically be pre-filled and sealed, or banded, before the surface is treated. As a result, it is not possible to use this process to make or commercialize hard capsule shells in a pre-locked status. Thus, the determination of the adequate filling parameters is left with the end user.

In an attempt to overcome these drawbacks, another technique used to impart enteric properties to hard or soft capsule shells involves the direct use of enteric polymers (acid-insoluble polymers) within the context of the hard shell manufacturing process. Thus, in this technique, the impartation of the enteric properties occurs during the manufacturing process as opposed to treating capsules which have already been pre-formed. However, when enteric polymers are used in large amounts, which are otherwise theoretically necessary for commercialization of the hard capsule shells manufacture, enteric polymers are poorly or completely water insoluble. Thus, the use of the process on a commercial scale raises a significant problem with respect to the effectiveness at which one can use this process under conventional dip moulding techniques. In addition, this method of coating works well on a small scale for hydroxypropyl methylcellulose (HPMC) capsules, but in the case of gelatin capsules, poor adhesion of the coat to the smooth gelatin surface can result in brittleness of the capsule. See, e.g., Huyghebaert et al., *Eur J Pharm Sci* 2004, 21, 617-623; Felton et al., *Pharm Sci* 2002, 4, Abstract T3320, and Thoma et al., *Capsugel Technical Bulletin* 1986, 1-16.

Attempts to overcome the deficiencies discussed above range from (i) using low, water-soluble amounts of acid-insoluble polymers in combination with major amounts of conventional film forming polymers; (ii) salifying all the acid groups of the water-insoluble polymers to obtain water-soluble derivatives; (iii) using solvent-based dipping solutions instead of water-based ones; and (iv) using alternative techniques, such as injection moulding, which do not require polymer solubilization. See e.g., WO 2004/030658; WO2008/119943; EP1447082; U.S. Pat. Nos. 4,138,013; 2,718,667; JP347246; WO2011/155686; JP2006016372; Han et al., *Journal of Pharmaceutical Sciences*, Vol. 98, No. 8, August 2009; and Kirilmaz L., S. T. P. *Pharma Sciences*, Nov. 10, 1993, 3/5 (374-378).

Despite this progress, many of the techniques described above still require the combination of enteric (acid insoluble polymer) and conventional non-enteric polymers, require salts or pH regulators leading to water sensitivity or brittleness of the resulting capsule shells, require multiple processing steps, and/or need to be processed in non-aqueous media. Thus, there is a need to develop a rapid, safe, and economic way to generate industrially viable hard capsule shells displaying enteric properties, while maintaining optimal chemical and mechanical properties, and without (i) the need for conventional film-forming polymers and/or non-aqueous media, or (ii) requiring additional processing steps, e.g., coating the enteric polymer, post-treatment or double dipping.

Accordingly, one aspect of the present disclosure provides aqueous-based compositions comprising partially neutralized hydroxypropyl methylcellulose acetate succinate (HPMCAS) polymer that display appropriate solid content, viscosity at room temperature, setting properties, and rheological behavior for use in the manufacture of capsule shells. As used in the present disclosure, "room temperature" refers to temperatures ranging from 15° C. to 25° C. and preferably 20° C. to 25° C.

In another aspect, the present disclosure relates to films and capsule shells obtained from the aforementioned water-based compositions, wherein the films and/or capsule shells display bulk enteric properties and exhibit optimal chemical and mechanical properties, e.g., disintegration profile, dissolution profile, film thickness, tensile strength values. In another aspect, the capsule shells and capsules made according to the processes of the present disclosure exhibit shapes similar to those of conventional capsule shells and capsules.

In another aspect, the present disclosure provides films and capsule shells displaying enteric properties, which are free of non-aqueous media/solvents.

In another aspect, the present disclosure provides rapid, economic, safe and easy to realize dip-moulding processes for the manufacture of hard capsule shells displaying bulk enteric properties (hereinafter also referred to as "enteric hard capsule shells"). In yet another aspect, the present disclosure provides a rapid, economic, safe and easy to realize "one step" dip-moulding process for the manufacture of hard capsule shells, wherein the co-presence of conventional film-forming non enteric polymers is no longer necessary.

In another aspect, the present disclosure provides processes for the manufacture of capsules and capsule shells wherein from a layer of dispersion, bulk evaporation of water occurs while the polymer particles flocculate (pack together), then close-pack letting water-filled interstices as per continuing evaporation and particle compaction, polymer film start forming with compacted (deformed) particles, leading to inter-particles diffusion of polymer molecules that generate isotropic polymer film (coalescence).

As used in the present disclosure, the following words, phrases, and symbols are generally intended to have the meanings as set forth below, except to the extent that the context in which they are used indicates otherwise.

As used herein, "optional" or "optionally" means that the subsequently described event or circumstance may or may not occur, and that the description includes instances where the event or circumstance occurs and instances in which it does not.

As used herein, "w/w %" means by weight as a percentage of the total weight.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

As used herein, "alkaline material" refers to at least one basic compound or basic composition capable of neutralizing succinic acid groups on HPMCAS, including but not limited to basic hydroxide compounds such as potassium hydroxide (KOH), sodium hydroxide (NaOH), calcium hydroxide ($Ca(OH)_2$), or other basic compounds or compositions, for example, ammonium hydroxide, cationic polymers such as EUDRAGIT® E PO; and mixtures thereof.

Unless otherwise indicated, "hydroxypropyl methylcellulose acetate succinate" polymer is also referred to as HPMCAS, and is commonly known in the field of polymers with the following alternative nomenclature: CAS registry number 71138-97-1; chemical common synonyms, such as: Hypromellose Acetate Succinate; HPMC-AS; Cellulose, 2-hydroxypropylmethylether, acetate, hydrogen butanedioate. Examples of the product include HPMCAS also known as Shin-Etsu AQOAT®. The polymer is available in micronized grade (LF, MF, HF) with mean particle size of 5 microns (µm) or granular grade (LG, MG, HG) with mean particle size of 1 mm. In certain embodiments the polymer is in the form of finely divided solid particles having an average diameter ranging from about 0.1 to about 10 microns. This example of HPMCAS is a product defined as containing not less than 4% and not more than 18% of succinoyl groups, which are only free carboxylic groups in the compound and not less than 5% and not more than 14% acetyl groups present in the compound. The degree of succinoyl and acetyl substitutions defines the grade (L, M or H), the higher the acetyl content, the lower the succinoyl content.

The term "solids" includes at least all non-aqueous ingredients present in the aqueous compositions, capsule shells, and capsules described herein. Other solids are discussed below in connection with optional ingredients of the aqueous compositions, capsule shells, and capsules described herein.

The terms "semi-neutralized" or "partially neutralized" indicate that only a portion of the succinic acid groups present in the HPMCAS polymer is neutralized with an alkaline material (such as a base), and the rest of the succinic acid groups remain in the acid form. Such partial neutralization is obtained by adding a base in a non-stoichiometric proportion, the molar quantity of acid groups being in excess versus the molar quantity of the base. The amount of alkaline material present in the aqueous composition may be expressed as an "alkali value." In certain embodiments such partial neutralization may be achieved with KOH in amounts lower than about 1.5 weight % of KOH equivalent based on the total weight of the aqueous composition. In certain embodiments, suitable amounts of KOH range from about 0.05 weight % to about 1.0 weight % of KOH equivalent based on the total weight of the aqueous composition. Neutralization of the HPMCAS polymer may alternatively be obtained by adding ammonia, for example in the form of aqueous ammonium hydroxide, or any other strong mineral base such as potassium, calcium or sodium hydroxide, or any polymeric alkaline material such as cationic polymers and copolymers, for example cationic copolymer EUDRAGIT® E PO based on poly(2-dimethylaminoethyl methacrylate-co-butyl methacrylate-co-methyl methacrylate) 2:1:1 (IUPCAC poly(butyl methacrylate-co-(2-dimethylaminoethyl)methacrylate-co-methyl methacrylate 1:2:1) commercially available from Evonik and having an alkali value of 0.18 g KOH/g polymer (a suitable amount was calculated to be 8.6% of Eudragit E PO (cationic polymer having an alkali value of 0.18 according to Evonik manufacturer), calculated from 8.6×0.18=1.55% of KOH equivalent). Neutral pH may be obtained by adding ammonia in amounts of 2.6% by weight of HPMCAS (see comparative example 4, 0.52 grams of ammonia (added as ammonium hydroxide) is added to 20 grams of HPMCAS i.e., 0.47 wt % of $NH_3$ on total composition weight i.e., 1.55 wt % of KOH equivalent based on the total weight of the aqueous composition, calculated from 0.47/17×56=1.55% of KOH equivalent, wherein the molar mass of $NH_3$=17 g/mol, molar mass of KOH=56 g/mol). Similarly, suitable amounts of other bases may be calculated from the KOH equivalent via this molar ratio.

Partial neutralization may be obtained in various ways. For example, partial neutralization may be obtained by adding ammonia in amounts of less than about 2.6% weight of total HPMCAS present in the aqueous composition, or by adding ammonia in amounts of less than about 2%, or less than about 1.5% of the amount of the total HPMCAS present in the aqueous composition. Partial neutralization may also be obtained by adding potassium hydroxide (KOH) in amounts of less than about 1.55% weight of total weight of the aqueous composition, or KOH in amounts of less than about 1.0%, or less than about 0.8% of total weight of the aqueous composition. Partial neutralization may further be obtained by adding cationic polymer EUDRAGIT® E PO in amounts of less than about 8.6% by weight of the total weight of the aqueous composition, or EUDRAGIT® E PO amounts of less than about 5.5%, or less than about 4.4% by weight of the total weight of the aqueous composition. Partial neutralization may also be obtained by adding a mixture of alkaline materials in total amount of less than about 1.55% by weight of KOH equivalent based on the total weight of the aqueous composition, or a mixture of alkaline materials in total amount of less than about 1.0% by weight of KOH equivalent, or less than about 0.8% weight of KOH equivalent based on the total weight of the aqueous composition.

The term "dispersion" refers to a two phase system where one phase consists of finely divided particles, often in a colloidal size range, distributed throughout a bulk substance. The particles are only partially soluble on the bulk substance. Upon application of the dispersion layer in the mold or pin used during capsule formation the colloidal particles come into direct contact with each other and form close-packed arrays due to water evaporation and the interfacial tension between water and polymer.

The hard capsules described herein have the same or similar shape of commercially available, conventional hard capsules intended for oral administration to human or animal subjects. The hard capsules described herein can be manufactured using different processes, such as the dip moulding processes discussed below as well as the use of conventional equipment. As is described in detail below, pin moulds may be dipped into an aqueous-based film forming composition and subsequently withdrawn. The film formed on the moulding pins surface can then be dried, stripped off the pins and cut to a desired length, thereby obtaining the capsules caps and bodies. Normally, caps and bodies have a side wall, an open end and a closed end. The length of the side wall of each of said parts is generally greater than the capsule diameter. The capsule caps and bodies may be telescopically joined together so as to make their side walls partially overlap and obtain a hard capsule shell.

As described herein, the term "partially overlap" is intended to encompass the side walls of caps and bodies having the same or similar length such that when a cap and a body are telescopically joined, the side wall of said cap encases the entire side wall of said body.

Unless otherwise indicated, "capsule" refers to filled capsule shells whereas "shell" specifically refers to an empty capsule. Since the hard capsule shells described herein can be filled with substances in liquid form, the hard capsules may be sealed or banded according to conventional techniques. Alternatively, the hard capsule shells can be manufactured to have a specific capsule shell design that provides certain advantages over conventional techniques, e.g., the ability to pre-lock empty caps and bodies, or completing the filling steps in a different location, or at a specific time. Examples of such designs may be found in, for example, WO 2009/138920 and WO 2009/050646.

The term "active ingredient" or "active pharmaceutical ingredient" (API) is used to indicate a component of the compositions, capsule shells, and capsules described herein that is pharmaceutically or physiologically active. Thus, it would be understood that any compound that is pharmaceutically or physiologically active, or that may take the benefit of delayed release, is considered to be an active ingredient. For example, acetaminophen, ibuprofen, or caffeine would be considered active ingredients. As used within this disclosure the term "active ingredient formulation" or "API formulation" refers to compositions or formulations comprising at least one active ingredient, and optionally other inactive components, such as excipients, additives, etc.

Unless otherwise indicated, "bulk enteric properties" means that the capsule shells described herein are soluble in, or disintegrated by alkaline intestinal secretions, but are substantially insoluble or resistant in acid secretions of the stomach. These enteric properties are intrinsic to the capsule shells and capsules as manufactured, i.e., no further coating or other post-manufacturing treatment is necessary to impart these enteric properties. Disintegration and dissolution properties can be tested according to monographs <701>, USP34-NF29, page 276; <711>, USP34-NF29, page 278; and <2040>, USP34-NF29, page 871.

In one embodiment, the present disclosure provides an aqueous composition for the manufacture of enteric capsule shells comprising HPMCAS polymer, wherein the polymer is partially neutralized to a pH with alkaline material.

In one embodiment, the present disclosure provides an aqueous composition for the manufacture of enteric capsule shells comprising HPMCAS polymer, wherein the polymer is partially neutralized to a pH ranging from 4 to 5.5. For instance, the pH range of 4.8 to 5.3 or 5 to 5.2.

In one embodiment, the present disclosure provides an aqueous composition for the manufacture of enteric capsule shells comprising HPMCAS polymer, wherein the polymer is partially neutralized to the extent that the enteric capsule shells manufactured with the aqueous solution are resistant to disintegration in demineralized water for at least 10 minutes, such as for example at least 15, 20, 25 or 30 minutes.

In one embodiment, the HPMCAS polymer is partly dispersed and partly solubilised in the aqueous media, in amounts ranging from about 15 w/w % to about 25 w/w % based on the total weight of the aqueous composition. The polymer is partially neutralized with less than about 0.5 w/w % of at least one alkaline material.

In one embodiment, HPMCAS is the only polymer displaying enteric properties in the aqueous compositions. Thus, in one embodiment the aqueous compositions do not contain other polymers, except HPMCAS, which display enteric properties, e.g., polymers such as polymethacrylates (copolymer of methacrylic acid and either methyl methacrylate or ethyl acrylate—e.g. Eudragit® enteric family members such as Eudragit® L); CAP (cellulose acetate phthalate); CAT (cellulose acetate trimellitate); HPMCP (hydroxypropyl methylcellulose phthalate); CMEC (Carboxy Methyl Ethyl Cellulose); or polyvinyl derivatives e.g. polyvinyl acetate phthalate (Coateric® family members).

One possible advantage of the aqueous compositions herein is that the HPMCAS amounts described allow for the manufacture of the hard capsule shells, e.g. using a dip-moulding process, without the need to incorporate other film-forming polymer(s) that are conventionally used as base film-forming polymers for hard capsule shells. In other words HPMCAS can be used along with the processing aids in amounts that provide films endowed with sufficient film forming properties such as thermal properties (DSC and MFT), thermo-rheological properties and mechanical properties (e.g. Young's module and brittleness). Accordingly, in one embodiment, the aqueous compositions may comprise film-forming polymer(s) conventionally used as base film-forming polymers for hard capsule shells in amounts less than about 5% by weight, e.g., less than about 1% by weight over the weight of the shell. Alternatively, in one embodiment, the aqueous compositions do not contain film-forming polymer(s) conventionally used as base film-forming polymers for hard capsule shells.

In one embodiment, film-forming polymer(s) conventionally used as base film-forming polymers for hard capsule shells include, for example, cellulose non enteric derivatives. Examples include HPMC (e.g. HPMC types 2910, 2906 and/or 2208 as defined in USP30-NF25), MC, gelatin, pullulan, PVA and non enteric starch derivatives, such as hydroxypropyl starch.

In one embodiment, the polymer is pre-dispersed in water and may include at least one dispersant. The amount of dispersant may range from about 0.5 w/w % to about 2 w/w %, based on the total weight of the aqueous composition. Non-limiting examples of dispersants include non-ionic emulsifiers or surfactants such as glyceryl esters (e.g. glyceryl monooleate and monolinoleate, medium chain triglycerides—i.e. $C_6$-$C_{12}$ fatty acid esters of glycerol); glycol esters (e.g. propylene glycol dicaprylocaprate and monolaurate); sorbitan monoesters (e.g. sorbitan monolaurate and monooleate); sorbitan polyoxyethylene esters (e.g. polyoxyethylene sorbitan monolaurate, monopalmitate, monostearate and monooleate); or mixtures of thereof. The dispersant may include sorbitan polyoxyethylene esters such as polysorbate (commercially known as Tween® 80).

In one embodiment, the aqueous composition comprises a gelling agent or gelling component that undergoes a thermal gelation at elevated temperature. In other words, the viscosity of said aqueous composition increases at a temperature above room temperature called critical gelation temperature (CGT) up to the point where the composition becomes a gel. The CGT depends on the gelling agent used and ranges from about 30° C. to 60° C.

In one embodiment, the gelling agent is selected from the group consisting of polyoxyethylene-polyoxypropylene-polyoxyethylene tri-block copolymers, cellulose derivatives, polysaccharides, and mixtures thereof. In one embodiment, the thermo-gelling agent consists of a non-ionic polyoxyethylene-polyoxypropylene-polyoxyethylene block polymer. This ingredient is also known in the field of polymers with the following synonyms: polyoxyethylene-propylene glycol copolymer, polyoxyethylene-polyoxypropylene copolymer, commercial names of families of polyoxyethylene-polyoxypropylene-polyoxyethylene block polymers are: LUTROL®, MONOLAN®, PLURONIC®, SUPRONIC®, SYNPERONIC®; CAS name α-Hydro-ω-hydroxypoly(oxyethylene)poly(oxypropylene)poly(oxyethylene) block copolymer; CAS number 9003-11-6. Examples of poloxamers may be found in, e.g., U.S. Pat. No. 3,740,421.

The language poloxamer or poloxamers refers to polyoxyethylene-polyoxypropylene-polyoxyethylene (POE)a-(POP)b-(POE)a triblock copolymers wherein a and b are integers and determined by the initial amounts of POE and POP used in the polymerization process as well as the polymerization process conditions. Within the average molecular weight ranging from about 1000 to about 20000, appropriate a/b ratios can be selected based on the desired hydrophilic/hydrophobic properties of the final polymer (since the POE blocks bring hydrophilicity whereas POP blocks bring hydrophobicity). Poloxamers suitable in the context of the present disclosure, include those for which the hydrophile-lipophile balance (HLB) of the hydrophilic and lipophilic moieties is higher than 5, such as higher than 7, and higher than 12.

In one embodiment, poloxamers are selected from those defined in the USP32-NF27 "poloxamers" monograph. Examples of such products are Poloxamer 124 (commercially available from BASF as KOLLISOLV® 124) AND POLOXAMER 188 (commercially available from BASF as PLURONIC® F68NF), having an average molecular weight range of about 2090 to about 2360, and from about 7680 to about 9510 respectively; and a polyethylene oxide ratio of about 45% to about 80% respectively. Mixtures of poloxamers, such as USP32-NF27 poloxamers, are also within the scope of the present disclosure In one embodiment, the thermo-gelling agent comprises, a polyoxyethylene-polyoxypropylene-polyoxyethylene tri-block polymer having an average molecular weight ranging from about 1000 to about 20000, said thermo-gelling agent being present in an amount ranging from about 0.1 w/w % to about 5 w/w % over the total weight of aqueous composition of the present disclosure.

In one embodiment, the thermo-gelling agent consists of a cellulose derivative selected from non-ionic products such as hydroxypropyl methylcellulose also known as HPMC (e.g. HPMC types 2910, 2906 and/or 2208 as defined in USP30-NF25); methyl cellulose (e.g. MC Metlose Sm from Shin Etsu); said thermo-gelling agent being present in an amount ranging from about 0.1 w/w % to about 5 w/w % over the total weight of aqueous composition of the present disclosure.

In one embodiment, the thermo-gelling agent consists of a polysaccharide selected from ionic products such as chitosan (poly(1,4)-2-amino-2-deoxy-D-glucan) with a deacetylation level above 70%; said thermo-gelling agent being present in an amount ranging from about 0.05 w/w % to about 2 w/w % over the total weight of aqueous composition of the present disclosure.

In another embodiment, the aqueous composition comprises a gelling agent that undergoes a cold gelation at low or room temperature. In other words, the viscosity of said aqueous composition increases at a temperature below or about room temperature called critical gelation temperature (CGT) down to the point where the composition becomes a gel. The CGT depends on the gelling agent used and ranges from about 0° C. to 25° C.

In one embodiment, the gelling agent includes polysaccharides or gums, such as carrageenan, gellan gum, guar gum, xanthan gum, andraganth gum, agar agar, pectin, curdlan, gelatine, furcellaran, tamarind seed, locust bean gum, or mixtures of thereof. The gelling agents may include carrageenan-Kappa (commercially available from Cargill) or gellan gum (commercially available from CP Kelco).

In one embodiment, the gelling agent consists of a polysaccharide in an amount ranging from about 0.1 w/w % to about 5 w/w % over the total weight of aqueous composition of the present disclosure.

In one embodiment, the aqueous compositions described herein may comprise one or more pharmaceutically acceptable agents, food acceptable colouring agents, or mixtures thereof.

Said agents may be selected from azo-, quinophthalone-, triphenylmethane-, xanthene- or indigoid dyes; iron oxides or hydroxides; titanium dioxide; or natural dyes and mixtures thereof. Further examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and Candurin® pearlescent pigments. Candurin® is manufactured and marketed by Merck KGaA, Darmstadt, Germany and consist of titanium dioxide and/or iron oxide—approved food and pharmaceutical colorants in many countries—and potassium aluminium silicate as color carrier. The latter is a natural, also widely approved, silicate also known under the name of "mica'."

In one embodiment, the pharmaceutically acceptable agents, food acceptable colouring agents, or mixtures thereof are present in an amount ranging from about 0 to about 5% by weight, e.g., from about 0 to about 2.5% by weight, and from about 0 to about 1.5% by weight over the total weight of the aqueous composition of the present disclosure.

In one embodiment, the aqueous compositions described herein further comprise at least one film forming aid.

In one embodiment, the term "film forming aid" comprises one or more plasticizers conventionally used in the manufacture of capsule shells, notably hard capsule shells, to ensure the formation of self-supported cohesive films and avoid capsule brittleness, and/or one or more viscosity enhancers, i.e. natural as well as synthetic substances conventionally used to optimize viscosity of aqueous compositions for the dip moulding manufacture of hard capsule shells. Film forming aids that display plasticizing properties include: phtalique esters (e.g. dimethyl-, diethyl-, dibutyl-, diisopropyl- and dioctyl-phtalate); citric esters (e.g. triethyl-, tributyl-, acetyltriethyl- and acetyltributyl-citrate); phosphoric esters (e.g. triethyl-, tricresyl, triphenyl-phosphate); alkyl lactate; glycerol and glycerol esters (e.g. glycerol triacetate also known as triacetine); sucrose esters; oils and fatty acid esters; butyl stearate; dibutyl sebacate; dibutyl tartrate; diisobutyl adipate, tributyrin; propylene glycol; polyethyleneglycol (PEG), polyoxyethylene (PEO); and mixtures thereof.

In one embodiment, film forming aids are selected from rheology modifiers, structuring agents, surfactants, plasticizers, and mineral charges e.g., hypromellose; alkyl cellulose (e.g. carboxy methylcellulose CMC) and other cellulosic derivatives (e.g. HPC, EC, MC, CMEC, HPMCP); polyvinyl acetate derivatives (PVAP); polysaccharides; glyceryl esters; glycol esters; sorbitan monoesters; sorbitan polyoxyethylene esters; polyoxyethylene (POE) ethers; glycerol; polyethylene glycols; polyols; fatty acid esters; glycerol polyethylene, glycol ricinoleate; macrogolglycerides; sodium lauryl sulfate (SLS); triethyl citrate (TEC); acetyl trialkyl citrate; glycerol triacetate (triacetine); alkyl phthalate; talc; silica (Syloid 244FP from Grace) and mixtures thereof.

In one embodiment, film forming aids that display both plasticizing and viscosity enhancing properties are selected from: glyceryl esters (e.g. glyceryl monooleate and monolinoleate, medium chain triglycerides—i.e. $C_6$-$C_{12}$ fatty acid esters of glycerol); glycol esters (e.g. propylene glycol dicaprylocaprate and monolaurate); sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; polyethylene glycols (e.g. PEG 4000, PEG 6000); glycerol polyethylene glycol ricinoleate; linoleoyl macrogolglycerides; sucrose esters; silica and mixtures thereof.

In one embodiment, film forming aids are selected from: sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; polyvinyl acetate derivatives (PVAP), cellulosic derivative (e.g. HPMC, HPC, EC, MC, CMEC, HPMCAS, HPMCP), silica and mixtures thereof.

In one embodiment, film forming aids are present in the aqueous composition in an amount ranging from about 0 to about 20% by weight, such as about 0 to about 15% by weight, about 0 to about 10% by weight over the total weight of the aqueous composition of the present disclosure.

In one embodiment, the water is purified in a manner that is acceptable for pharmaceutical uses as defined under USP purified water in USP32 and USP34-NF29. It will be understood that the aqueous composition described herein allow for non-aqueous solvents in trace amounts. Typical non-aqueous solvents are for example ethanol, or other low MW alcohols conventionally used as solvents, chlorinated solvents, ethers.

In one embodiment, the present disclosure also provides capsule shells comprising the aqueous compositions described herein, for example, as bulk enteric hard capsule shells.

In one embodiment, hard capsule shells are obtainable using the aqueous compositions disclosed above and the processes as disclosed below, e.g., dip moulding.

In one embodiment, the hard capsule shells as described comprise a shell thickness (after drying to bring the water content of the shell below 6% by weight over the weight of the shell) lower than about 250 μm, e.g., at about 150 μm, and at about 70 μm. Thus, in one embodiment, the shell thickness may range from about 70 to about 150 μm.

It should be noted that the aforementioned shell thickness values are difficult, if not impossible, to be obtain with manufacturing methods that are alternative to dip moulding. For example, injection moulding techniques typically produce shell thicknesses of about 300 to about 500 μm.

In one embodiment, the shells may or may not be externally coated with additional one or more polymer layers. Alternatively, the shells are monolayer, i.e., no external additional polymer layers are present. Thus, in one embodiment, no additional functional polymer layers are present.

Unless otherwise indicated, functional polymer layers means layers containing functional polymers that impart a particular mechanical or chemical properties to the coated shell. Functional polymers are enteric polymers conventionally used to coat pharmaceutical solid dosage forms and/or colonic release polymers (i.e. polymers used to achieve disintegration of the coated dosage form in the colon region of a subject). An overview of these polymers as applied to hard capsule coatings, can be found in, for example, WO 2000/018377. Capsule banding or sealing are not presently considered as applying additional external layer(s), hence banded or sealed capsule shells and capsule are well within the scope of the present disclosure.

In one embodiment, the present disclosure provides bulk enteric hard capsule shells comprising hydroxypropyl methyl cellulose acetate succinate (HPMCAS) polymer, at least one gelling agent, at least one dispersant and water, wherein the polymer is partially neutralized with at least one alkaline material.

Typical amounts of water are below 20% by weight over the total weight of the shell, such as below 10% by weight, below 8% by weight, and below 6% by weight over the total weight of the shell.

In one embodiment, the amount of water, as equilibrated with the relative humidity of the outside air, ranges from about 2% to about 20% by weight of the total weight of the capsule shell.

In one embodiment, the hard capsule shells further comprise at least one encapsulated active ingredient. Thus, the capsules may be filled with one or more acid-instable substances and/or one or more substances associated with gastric side effects in humans and/or animals.

In one embodiment, acid-instable substances are natural or synthetic substances that undergo chemical degradation or modification in the acid environment present in the stomach of a subject. In one embodiment, substances associated with gastric side effects are pharmaceutical drugs or compositions intended for human or animal oral administration, whose release in the stomach upon oral administration to a human or animal being is associated to gastric side-effects, such as gastric reflux or impairment of physiological and/or structural integrity of gastric mucosa (e.g. stomach ulcers).

In one embodiment, the at least one active ingredient comprises a solid, semi-solid, or liquid form.

In one embodiment, the shells further comprise one or more pharmaceutically or food acceptable colouring agents, as defined above. One or more pharmaceutically acceptable agents or food acceptable colouring agents are present in amounts ranging from 0 to about 15% by weight, such as, from 0 to about 10% by weight and from 0 to about 8% by weight over the total weight of the shells.

In one embodiment, the shells comprise a gelling agent as defined above. Gelling agent may be present in amounts ranging from 0% to about 40% by weight, such as, from 0% to about 30% by weight and from 0% to about 25% by weight over the total weight of the shells.

In one embodiment, the shells comprise a dispersant as defined above. Dispersant may be present in amounts ranging from 0% to about 20% by weight, such as, from 0% to about 10% by weight and from 0% to about 5% by weight over the total weight of the shells.

In one embodiment, the shells further comprise a film forming aid as defined above. Film forming aids may be present in amounts ranging from 0% to about 40% by weight, such as, from 0% to about 30% by weight and from 0/o to about 25% by weight over the total weight of the shells.

In one embodiment, the present disclosure also provides a capsule shell comprising an aqueous dispersion of a functional hydroxypropyl methyl cellulose acetate succinate (HPMCAS)polymer, said polymer being present in an amount ranging from about 15% to about 25% by weight of the total weight of said aqueous composition, wherein the polymer is partially neutralized with at least one alkaline material; at least one dispersant present in an amount ranging from about 0.5% to about 2% by weight of the total weight of said aqueous composition; at least one gelling agent present in an amount ranging from about 0.1% to about 5% by weight of the total weight of said aqueous composition; at least one film forming aid present in an amount ranging from about 0% to about 40% by weight of the total weight of said aqueous composition; and water.

In one embodiment, the present disclosure also provides hard capsule shells and processes for making the hard capsule shells described herein, wherein the capsule shells comprise a disintegration release of less than about 10% of the total encapsulated at least one active ingredient after a time of about 2 hours and about pH 1.2

In another embodiment, the present disclosure also provides hard capsule shells and processes for making the hard capsule shells described herein, wherein the capsule shells comprise a dissolution release of less than about 10% of the total encapsulated at least on active ingredient after at time of about 2 hours and about pH 1.2

In one embodiment, the hard capsule shells comprise a disintegration release of less than about 10% of the total encapsulated at least one active ingredient after a time of about 2 hours and about pH 1.2 and a dissolution release of less than about 10% of the total encapsulated at least on active ingredient after at time of about 2 hours and about pH 1.2.

In one embodiment, the dissolution release is about 80% of the total encapsulated at least one active ingredient at a time of about 45 minutes and about pH 6.8

In one embodiment, capsule shells have bulk enteric properties when they have dissolution and disintegration profiles that at least match the disintegration and dissolution profiles reported above. These disintegration and dissolution profiles in enteric media are difficult if not impossible to be achieved by capsule shells obtained using water based compositions containing lower amounts of enteric polymer. Because conventional use has been to use the enteric polymer in solution and not the described dispersion, the use of much lower amounts of enteric polymer was a considered to be a mandatory feature, which does not apply here.

In one embodiment, the present disclosure also provides hard capsule shells and processes for making the hard capsule shells described herein, wherein the capsule shells comprise a dissolution release of less than about 10% of the total encapsulated at least one active ingredient after a time of about 2 hour in demineralised water at about pH 5.5. Although possible by using enteric polymers in solution, this resistance to dissolution in demineralised water is difficult if not impossible to be achieved by capsule shells obtained using fully neutralized enteric polymers in water-based compositions, because of salt water-sensitivity, which does not apply to the partially neutralized dispersion described here.

The described filled capsules may be made tamper-proof by using appropriate techniques to make the joint permanent. Typically, sealing or banding techniques can be used where these techniques are well-known to any skilled person in the field of capsules. In this connection, it is conventional practice to perform banding and/or sealing using polymer solutions in water/ethanol or water/isopropanol solutions. Traces of such non water solvents can be found if an elemental analysis is performed on a sealed or banded capsule without making a distinction between ingredients that are part of the shell and ingredients that are part of the band or sealing subsequently applied.

Processes to make the aforementioned capsule shells and capsules comprising the aqueous composition described herein are also disclosed. Despite the high solid content, the aqueous compositions described herein have a medium viscosity when the HPMCAS is in a dispersed state and not in solution.

In one embodiment, the viscosity of the aqueous compositions described herein, when measured at 21° C. with a Brookfield viscosimeter equipped with a spindle 27 at a speed of 10 RPM, ranges from about 1 cP to about 5000 cP, e.g., from about 500 cP to about 3000 cP, and from about 1000 cP to about 2500 cP.

In one embodiment the minimum film-forming temperature (MFFT) of the aqueous compositions described herein, when measured with a conventional MFFT-bar from Rhopoint, ranges from about 10° C. to 80° C., e.g., from about 20° C. to 70° C. or about 30° C. to 70° C. The MFFT described the temperature from which the film starts to coalesce. Without being bound to any theory, it is believed that the aqueous composition described here undergoes a mixed drying process combining coalescence of polymer particles and gelation of the gelling agent. Both physical features define the adequate temperature at which the film adheres on the pin without flowing down on after dipping, known as the setting temperature. This setting temperature is a parameter of aqueous compositions to be used in the manufacture of hard capsules that is well known to any skilled person.

In one embodiment, the aqueous compositions to be used in the context of the dip-moulding processes described below are the aqueous compositions as discussed above. Accordingly, any consideration and embodiment discussed in connection with the aqueous compositions apply to the dip-moulding processes described herein to the extent that it is technically possible.

Accordingly, in one embodiment, the present disclosure provides thermo-gelling dip-moulding processes for the manufacture of bulk enteric hard capsule shells when the aqueous composition comprises a thermo-gelling agent, wherein the processes comprise:

a) providing an aqueous composition comprising hydroxypropyl methyl cellulose acetate succinate (HPMCAS) polymer, a thermo-gelling agent, a dispersant and water, wherein the water-dispersed polymer is partially neutralized with alkaline material
b) adjusting said aqueous composition to a temperature (T1) ranging from about 5° C. to about 40° C.;
c) pre-beating moulding pins to a dipping temperature (T2) ranging from about 15° C. to about 70° C. higher than said temperature T1;
d) dipping the pre-heated moulding pins into said matured aqueous composition at temperature T1;
e) forming a film on said moulding pins by withdrawing said pins from said aqueous composition; and
f) drying the film on said moulding pins to form bulk enteric hard capsule shells.

In one embodiment, the aqueous composition is kept in step (b) at a temperature ranging from about 5° C. to about 40° C., such as, for example from about 15° C. to about 35° C. and about 20° C. to about 30° C.

In one embodiment, pins are pre-heated and dipped at a temperature ranging from about 15° C. to about 70° C. higher than the temperature of the aqueous composition in step (b). For example, the temperature may range from about 15° C. to about 50° C. and from about 25° C. to about 50° C. higher than the temperature of the aqueous composition in step (b). In one embodiment, pins are pre-heated to a temperature ranging from about 45° C. to about 90° C.

In another embodiment, the present disclosure provides cold gelation dip-moulding processes for the manufacture of bulk enteric hard capsule shells when the aqueous composition comprises at least one gelling agent, wherein the processes comprise:

a') providing an aqueous composition comprising hydroxypropyl methyl cellulose acetate succinate (HPMCAS) polymer, a gelling agent, a dispersant and water, wherein the water-dispersed polymer is partially neutralized with alkaline material,
b') adjusting said aqueous composition to a temperature (T3) ranging from about 30° C. to about 80° C.;
c') pre-heating moulding pins to a dipping temperature (T4) ranging from about 5° C. to about 30° C.;
d') dipping the pre-heated moulding pins into said matured aqueous composition;
e') forming a film on said moulding pins by withdrawing said pins from said aqueous composition; and
f') drying the film on said moulding pins to form bulk enteric hard capsule shells.

In one embodiment, the aqueous composition is kept in step (b') at a temperature T3 ranging from about 30° C. to about 80° C., preferentially from about 30° C. to about 60° C. and more preferentially from about 40° C. to about 60° C.

In one embodiment, pins are pre-heated and dipped at a temperature T4 ranging from about 5° C. to about 30° C. preferentially from about 10° C. to about 30° C. and more preferentially from about 15° C. to about 25° C.

In one embodiment, step (d) comprises a single dipping of the pins. In other words, no multiple dipping of the pins is necessary to obtain a pick-up of material on pins surface sufficient to obtain a film endowed with required mechanical properties.

In one embodiment, step (f) of drying is performed according to drying techniques typically applied in the field of hard capsules, which can be accomplished using equipment known to the skilled person for this purpose. In one embodiment, step (f) of drying can be performed according to any technique commonly known for this purpose, for example by placing the pins in ovens. In one embodiment, step f) of drying is performed at a temperature ranging from about 20° C. to about 90° C.

In one embodiment, the moulding processes further comprise a step (g) of filling hard capsules shells with one or more substances as disclosed above.

In one embodiment, the moulding processes further comprise a step (h) of making a filled hard capsule tamper-proof by sealing and/or banding the filled hard capsule obtained in step (g).

EXAMPLES

A suitable test procedure to test disintegration properties of the shells (and capsules) is as follows: USP Apparatus basket-rack assembly consisting of six open-ended transparent tubes, each tube being provided with a disk; Disintegration media: simulated gastric fluid at pH 1.2 with NaCl for 2 hours then simulated intestinal fluid at pH 6.8 with $KH_2PO_4$+NaOH; Test conditions: fluid kept at 37° C.; oscillation frequency is 30 minutes; volume of disintegration medium is 800 ml; number of samples tested is 6. Test shells #0 are pre-filled with 450 mg of acetaminophen. Capsules are placed in the tubes and a disk is over imposed. The basket is then placed in the simulated gastric fluid for 2 hours and then moved to the simulated intestinal fluid. UV ($\lambda$=300 nm) is used to quantify dissolved acetaminophen (as % of filled amount) in both simulated gastric and intestinal fluids.

A suitable test procedure for dissolution properties of the shells (and capsules) is as follows:

USP Dissolution Apparatus 2 (paddle), dissolution media: simulated gastric fluid at pH 1.2 0.1 N HCl for 2 hours then simulated intestinal fluid at pH 6.8 with $Na_3PO_4$; Test conditions: fluid kept at 37° C., paddle vessel (USP/NF) of cylindrical form with spherical end; rotation speed was 50 rpm; dissolution liquid volume is 750 ml; number of samples is 6. Test shells #0 are filled with 380 mg of acetaminophen. Capsules are then placed into the vessel which is placed in the simulated gastric fluid for 2 hours. Subsequently, 250 ml of 0.20 M tribasic sodium phosphate are added to simulated intestinal fluid pH 6.8. UV (l=300 nm) is used to quantify dissolved acetaminophen (as % of filled amount) in the dissolution media. Measures are made every 15 minutes when in the simulated gastric fluid and every 3 minutes in the simulated intestinal fluid.

When tested according to USP32-NF27 monographs <701> and <711> for delayed-release dosage forms, respectively, the capsule shells once filled with acetaminophen showed at least the following profiles:

Disintegration: release less than 10% of total encapsulated acetaminophen after 2 hours at pH 1.2; and Dissolution: release less than 10% of total encapsulated acetaminophen after 2 hours at pH 1.2, where 80% of the acetaminophen was released after 45 minutes at pH 6.8.

A suitable test procedure for demineralised water-resistance properties of the shells (and capsules) is as follows: USP Dissolution Apparatus 2 (paddle); dissolution media: demineralised water at pH about 5.5 for 2 hours; Test conditions: fluid kept at 37° C., paddle vessel (USP/NF) of cylindrical form with spherical end; rotation speed was 50 rpm; dissolution liquid volume is 750 ml; number of samples is 6. Test shells #0 are filled with 380 mg of acetaminophen. Capsules are then placed into the vessel which is placed in the demineralised water for 1 hour. UV (λ=300 nm) is used to quantify dissolved acetaminophen (as % of filled amount) in the dissolution media. Measures are made every 15 minutes. The capsule shells once filled with acetaminophen showed at least the following dissolution profiles: release less than 10% of total encapsulated acetaminophen after 2 hours in demineralised water.

Description of the Test Protocols a) Determination of the Ability for the Aqueous Dispersion to Form a Continuous Film:

The prepared aqueous dispersion is casted on a glass plate kept at the setting temperature of the composition using Capsugel film cast equipment (modified motorized Thin Layer Chromatography Plate Coater unit from CAMAG) or any other conventional drawdown coating equipment to make a uniform thin film having a dry thickness of about 100 μm. The casted film on the glass plate is kept in an oven during 1 hour at the drying temperature, and then stored for at least 2 hours at room temperature and 50% RH to allow full drying. Once dried, the obtained film is removed from the glass plate and evaluated for visual, physical properties, and thermal properties. The Tg and the MFFT of the prepared aqueous composition are also measured with respectively DSC equipment and MFFT-bar, as per standard operating procedures for films and coating evaluation.

b) Evaluation of the Aqueous Dispersion Setting Properties

To reproduce the capsule dipping process, a simplified lab-scale equipment called Pin Lab Dipper has been developed to mimic the dipping of a pin into the solution. This device is equipped with an electronically-assisted module to control the pin dipping profile and withdrawal profile. It also ensures the pin rotation to the upright position and regulates the pin temperature. The dipping step is followed by a drying sequence with appropriate hot air. This test evaluates the potential setting properties of the tested solutions, whether it is possible to form a continuous and homogeneous film on the stainless steel pin by dip moulding processes.

Example 1: Preparation of an Aqueous Dispersion Comprising a Thermo-Gelling Agent The composition was made according to Table 1.

TABLE 1

| | wt (g) | wt % | solids | non-vol % | Process step |
|---|---|---|---|---|---|
| water | 80.00 | 74.23 | 0.00 | 0.00 | |
| HPMCAS | 20.00 | 18.56 | 18.56 | 78.74 | |
| Tween 80 | 1.20 | 1.11 | 1.11 | 4.72 | 1: dispersant |
| NH3 | 0.20 | 0.19 | 0.19 | 0.79 | 2: partial neutralization |
| water | 0.37 | 0.34 | 0.00 | 0.00 | |
| triacetine | 2.00 | 1.86 | 1.86 | 7.87 | 3: film-forming aid |
| Poloxamer | 2.00 | 1.86 | 1.86 | 7.87 | 4: thermo-gelling agent |
| water | 2.00 | 1.86 | 0.00 | 0.00 | |
| Total | 107.77 | 100.00 | 23.57 | 100.00 | |

Example 2: Preparation of an Aqueous Dispersion Comprising a Gelling Agent

The composition was made according to Table 2.

TABLE 2

| | wt (g) | wt % | solids | non-vol % | Process step |
|---|---|---|---|---|---|
| water | 80.00 | 64.56 | 0.00 | 0.00 | |
| HPMCAS | 20.00 | 16.14 | 16.14 | 83.54 | |
| Tween 80 | 1.20 | 0.97 | 0.97 | 5.01 | 1: dispersant |
| NH3 | 0.20 | 0.16 | 0.16 | 0.84 | 2: partial neutralization |
| water | 0.37 | 0.30 | 0.00 | 0.00 | |
| triacetine | 2.00 | 1.61 | 1.61 | 8.35 | 3: film-forming aid |
| Carrageenan Kappa | 0.40 | 0.32 | 0.32 | 1.67 | 4: gelling agents |
| KCl | 0.14 | 0.11 | 0.11 | 0.58 | |
| water | 19.60 | 15.82 | 0.00 | 0.00 | |
| Total | 123.91 | 100.00 | 19.32 | 100.00 | |

Example 3: Preparation of an Aqueous Dispersion Comprising Mixture of Alkaline Materials The composition was made according to Table 3.

TABLE 3

| | wt (g) | wt % | solids | non-vol % | Process step |
|---|---|---|---|---|---|
| water | 80.00 | 73.94 | 0.00 | 0.00 | |
| HPMCAS | 20.00 | 18.48 | 18.48 | 77.43 | |
| Tween 80 | 1.20 | 1.11 | 1.11 | 4.65 | 1: dispersant |
| Eudragit E PO | 0.43 | 0.40 | 0.40 | 1.66 | |
| NH3 | 0.20 | 0.18 | 0.18 | 0.77 | 2: partial neutralization |
| water | 0.37 | 0.34 | 0.00 | 0.00 | |
| triacetine | 2.00 | 1.85 | 1.85 | 7.74 | 3: film-forming aid |
| Poloxamer | 2.00 | 1.85 | 1.85 | 7.74 | 4: thermo-gelling agent |
| water | 2.00 | 1.85 | 0.00 | 0.00 | |
| Total | 108.20 | 100.00 | 23.87 | 100.00 | |

Comparative Example 4: Preparation of a Fully Neutralised Aqueous Dispersion with Conventional Film-Forming Polymer The composition was made according to Table 4.

TABLE 4

|  | wt (g) | wt % | solids | non-vol % | Process step |
|---|---|---|---|---|---|
| water | 80.00 | 72.28 | 0.00 | 0.00 | |
| HPMCAS | 20.00 | 18.07 | 18.07 | 77.76 | |
| Tween 80 | 1.20 | 1.08 | 1.08 | 4.67 | 1: dispersant |
| NH3 | 0.52 | 0.47 | 0.47 | 2.02 | 2: full neutralization |
| water | 0.97 | 0.87 | 0.00 | 0.00 | |
| HPMC | 4.00 | 3.61 | 3.61 | 15.55 | 3: conventional film-forming polymer |
| water | 4.00 | 3.61 | 0.00 | 0.00 | |
| Total | 110.69 | 100.00 | 23.24 | 100.00 | |

Comparative Example 5: Preparation of a Fully Neutralised Aqueous Dispersion with Conventional Film-Forming Polymer The composition was made according to Table 5.

TABLE 5

|  | wt (g) | wt % | solids | non-vol % | Process step |
|---|---|---|---|---|---|
| water | 80.00 | 73.61 | 0.00 | 0.00 | |
| HPMCAS | 20.00 | 18.40 | 18.40 | 77.76 | |
| Tween 80 | 1.20 | 1.10 | 1.10 | 4.67 | 1: dispersant |
| NH3 | 0.52 | 0.48 | 0.48 | 2.02 | 2: full neutralization |
| water | 0.97 | 0.89 | 0.00 | 0.00 | |
| triacetine | 2.00 | 1.84 | 1.84 | 7.78 | 3: film-forming aid |
| Poloxamer | 2.00 | 1.84 | 1.84 | 7.78 | 4: thermo-gelling agent |
| water | 2.00 | 1.84 | 0.00 | 0.00 | |
| Total | 108.69 | 100.00 | 23.66 | 100.00 | |

Results

Table 6 provides the resulting viscosity, water resistance and flexibility results for Examples 1-5.

TABLE 6

| example # | viscosity | demineralised water-resistance | flexibility |
|---|---|---|---|
| 1 | 1040 cp | good | good |
| 2 | 500 cp | good | fine |
| 3 | 1000 cp | good | fine |
| comparative 4 | 1200 cp | poor | brittle |
| comparative 5 | 500 cp | poor | brittle |

Viscosity: Measured with Brookfieldn spindle 27, 10 RPM, 21° C.
Demineralised water-resistance was determined as described previously in the test procedure. The resulting responses were rated according to the following scale as to range: poor (film dissolution below 30 minutes), medium (film dissolution between 30 minutes and 1 hour), fine (film dissolution between 1 hour and 2 hours), good (test passed, film dissolution after 2 hours). Flexibility: deformation assessment of the film. Range: poor (=brittle film), medium (=fragile film), fine (=handleable film), good (=flexible film)

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule shell made from a composition comprising:
an aqueous composition comprising a dispersion of hydroxypropyl methyl cellulose acetate succinate (HPMCAS) polymer dispersed in water, wherein the polymer is present in an amount ranging from about 15% to about 25% by weight of the total weight of the aqueous composition;
at least one dispersant in an amount ranging from about 0.5% to about 2% by weight of the total weight of said aqueous composition;
at least one gelling agent present in an amount ranging from about 0.1% to about 5% by weight of the total weight of said aqueous composition;
water; and
wherein the dispersed polymer is partially neutralized with less than 0.5 w/w% of at least one alkaline material based on the total weight of the aqueous composition.

2. The capsule shell according to claim 1, further comprising at least one film forming aid in an amount ranging from about 1.6% to about 40% by weight, of the total weight of the aqueous composition.

3. The capsule shell according to claim 1, wherein the capsule shell is a hard capsule shell.

4. The capsule shell according to claim 1, wherein the amount of water, as equilibrated with the relative humidity of the outside air, ranges from about 2% to about 20% by weight of the total weight of the capsule shell.

5. The capsule shell according to claim 1, further comprising at least one encapsulated active ingredient.

6. The capsule shell according to claim 1, wherein the at least one active ingredient comprises a solid, semi-solid, or is in a liquid form.

7. The capsule shell according to claim 1, wherein the capsule exhibits a disintegration release of less than about 10% of the total encapsulated at least one active ingredient after a time of about 2 hours at a pH of about 1.2; or a dissolution release of less than about 10% of the total encapsulated at least one active ingredient after at time of about 2 hours at a pH of about 1.2.

8. The capsule shell according to claim 1, wherein the capsule exhibits a dissolution release of less than about 10% of the total encapsulated at least one active ingredient after a time of about 45 minutes in demineralized water.

9. The capsule shell according to claim 1, wherein the capsule exhibits a dissolution release of about 80% of the total encapsulated at least one active ingredient at a time of about 45 minutes at a pH of about 6.8.

10. A capsule shell comprising:
hydroxypropyl methyl cellulose acetate succinate (HPMCAS) polymer, wherein the polymer is partially neutralized with 0.84 w/w% or less of at least one alkaline material based on the total weight of the capsule shell;
at least one dispersant in an amount ranging from about 0.5% to about 20% by weight of the total weight of the capsule shell;
at least one thermogelling agent present in an amount ranging from about 0.1% to about 40% by weight of the total weight of the capsule shell, wherein the thermogelling agent is capable of undergoing a thermal gelation at an elevated temperature of from about 30° C. to about 80° C.; and water in an amount from about 2% wt to about 20% wt of the total weight of the capsule shell.

11. The capsule shell of claim 10, further comprising at least one film forming aid in an amount ranging up to about 40% by weight, of the total weight of the capsule shell.

12. The capsule shell of claim 10, wherein the capsule shell is a hard capsule shell.

13. The capsule shell of claim 10, wherein the amount of water, as equilibrated with the relative humidity of the outside air is less than about 10% by weight of the total weight of the capsule shell.

14. The capsule shell according to claim 10, wherein the capsule shell exhibits a disintegration release of less than about 10% of a total encapsulated at least one active ingredient after a time of about 2 hours at a pH of about 1.2.

15. The capsule shell according to claim 10, wherein the capsule shell exhibits a disintegration release of less than about 10% of a total encapsulated at least one active ingredient after at time of about 2 hours at a pH of about 1.2.

16. The capsule shell according to claim 10, wherein the capsule shell exhibits a dissolution release of less than about 10% of a total encapsulated at least one active ingredient after a time of about 45 minutes in demineralized water.

17. The capsule shell according to claim 10, wherein the capsule shell exhibits a dissolution release of about 80% of a total encapsulated at least one active ingredient at a time of about 45 minutes at a pH of about 6.8.

* * * * *

UNITED STATES PATENT AND TRADEMARK OFFICE
CERTIFICATE OF CORRECTION

| | | |
|---|---|---|
| PATENT NO. | : 10,898,440 B2 | Page 1 of 1 |
| APPLICATION NO. | : 16/660714 | |
| DATED | : January 26, 2021 | |
| INVENTOR(S) | : Cade et al. | |

It is certified that error appears in the above-identified patent and that said Letters Patent is hereby corrected as shown below:

In the Claims

Column 18, Line 46, "after at time of" should read --after a time of--.

Column 19, Line 22, "after at time of" should read --after a time of--.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*